United States Patent
Hanes et al.

(10) Patent No.: US 7,217,538 B2
(45) Date of Patent: *May 15, 2007

(54) **CAESS1: A *CANDIDA ALBICANS* GENE, METHODS FOR MAKING AND USING, AND TARGETING IT OR ITS EXPRESSION PRODUCTS FOR ANTIFUNGAL APPLICATIONS**

(75) Inventors: Steven D Hanes, Albany, NY (US); Gina Devasahayam, Madras (IN); Vishnu Chaturvedi, Slingerlands, NY (US)

(73) Assignee: Health Research Incorporated, Reusselger, NY (US)

( * ) Notice: Subject to any disclaimer, the term of this patent is extended or adjusted under 35 U.S.C. 154(b) by 357 days.

This patent is subject to a terminal disclaimer.

(21) Appl. No.: 10/342,555

(22) Filed: Jan. 15, 2003

(65) Prior Publication Data

US 2003/0143615 A1    Jul. 31, 2003

Related U.S. Application Data

(62) Division of application No. 09/507,242, filed on Feb. 18, 2000, now Pat. No. 6,537,753.

(51) Int. Cl.
*C12P 21/00* (2006.01)
*C12Q 1/68* (2006.01)
*C12N 1/00* (2006.01)
*C07K 1/00* (2006.01)
*A61K 39/00* (2006.01)

(52) U.S. Cl. .................... 435/69.1; 435/6; 435/69.7; 435/320.1; 435/255.4; 435/254.22; 435/254.1; 435/252.3; 435/243; 424/274.1; 530/350; 536/23.1; 536/23.2; 536/23.74; 536/24

(58) Field of Classification Search ............... 435/6, 435/243, 252.3, 254.1, 254.2, 255.4, 320.1, 435/69.1, 69.7, 254.22; 424/274.1; 530/350; 536/23.1, 23.2, 23.74, 24.32, 24
See application file for complete search history.

(56) References Cited

U.S. PATENT DOCUMENTS

| 5,489,513 | A | 2/1996 | Springer et al. |
| 6,537,753 | B1 * | 3/2003 | Hanes et al. .................... 435/6 |
| 6,747,137 | B1 * | 6/2004 | Weinstock et al. ......... 536/23.1 |

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129-2138, 1990.*
Lazar et al., Molecular and Cellular Biology, 8(3): 1247-1252, 1988.*
Jobling et al. (Mol. Microbiol. 1991, 5(7): 1755-67).*
Accession No. AA182274 (Jan. 6, 1997).
Accession No. Y13120 (May 27, 1997).
Ahn AH, Kunkel LM. The structural and functional diversity of dystrophin. Nat Genet. Apr. 1993;3(4):283-91.
Cawthon RM, Andersen LB, Bachberg AM, Xu GF, O'Connell P, Viskochil D, Weiss RB, Wallace MR, Marchuk DA, Culver M, et al. cDNA sequence and genomic structure of EV12B, a gene lying within an intron of the neurofibromatosis type 1 gene. Genomics. Mar. 1991;9(3):446-60.
Houghten et al. (Vaccines, 1986, Edited by Fred Brown: Cold Spring Harbor Laboratory.
Bowie JU, Reidhaar-Olson JF, Lim WA, Sauer RT. Deciphering the message in protein sequences: tolerance to amino acid substitutions. Science. Mar. 16, 1990;247(4948):1306-10.
Li Z, Li H, Devasahayam G, Gemmill T, Chaturvedi V, Hanes SD, Van Roey P. The structure of the *Candida albicans* Ess1 prolyl isomerase reveals a well-ordered linker that restricts domain mobility. Biochemistry. Apr. 26, 2005;44(16):6180-9.

* cited by examiner

*Primary Examiner*—Mark Navarro
*Assistant Examiner*—Padma Baskar
(74) *Attorney, Agent, or Firm*—Thomas J. Kowalski; Frommer Lawrence & Haug LLP

(57) ABSTRACT

Disclosed and claimed is the CaESS1 gene, portions thereof such as primers or probes, expression products therefrom, and methods for using the gene, and expression products; for instance, for diagnostic, therapeutic or preventive compositions.

3 Claims, 5 Drawing Sheets

```
  1 GATCAACCAATAGATGTTGTTGCTAACCAAGTCAAAGACGCGTTGAAGACAAGAGGTATTTAGACACACAAGCATTAGTCACTGAAT  88
 89 AGATATACAGTTGAGATTCGTCTTGCAATAGATATTAAGGTAGTGTACATTTACCAAAACTTCTCTCTTTTTCTATATTCTTCATCAACACAAGATTTTC 188
189 GTTGTTGCCTTTTGTTGTATTATTGTCATCAGTTAGCTTGATTCTTTTTGCAGTAGTATATCATC ATG GCA TCG ACA TCA ACA GGC TTA  279
                                                                    M   A   S   T   S   T   G   L    8
280 CCA CCT AAT TGG ACG ATT AGA GTA TCC CAT AAC AAA GAG TAT TTC TTA AAC CAA TCT ACC AAT GAG TCG  354
  9 P   P   N   W   T   I   R   V   S   H   N   K   E   Y   F   L   N   Q   S   T   N   E   S   33

355 TCT GAC CCA CCT TAT GGC ACT GGC AAA GAA GTA TTG AAT GCA TAC ATT GCG AAG TTT AAA AAC AAT GGT TAC  429
 34 S   D   P   P   Y   G   T   G   K   E   V   L   N   A   Y   I   A   K   F   K   N   N   G   Y   58

430 AAG CCA CTT GTG AAT GAG GAT GGC CAG GTT AGA GTT TCT CAT TTG TTG ATC AAG AAC AAT CAA TCA AGA AAA CCC  504
 59 K   P   L   V   N   E   D   G   Q   V   R   V   S   H   L   L   I   K   N   N   Q   S   R   K   P   83

505 AAG TCT TGG AAG TCC CCA GAT GGT ATA AGT AGA ACT AGA GAC GAA TCT ATA CAG ATA TTG AAG AAA CAT TTG GAA  579
 84 K   S   W   K   S   P   D   G   I   S   R   T   R   D   E   S   I   Q   I   L   K   K   H   L   E  108

580 AGA ATA TTG AGT GGT GAG GTT AAA CTA AGT GAA TTG GCA AAT ACC GAA AGT GAT TGC AGC TCA CAT GAC AGA GGT  654
109 R   I   L   S   G   E   V   K   L   S   E   L   A   N   T   E   S   D   C   S   S   H   D   R   G  133

655 GGT GAT TTA GGG TTT TTT AGC AAA GGA CAA ATG CAA TTC GAA GAA GCC GCA TTC AAT TTG CAT GTT GGA  729
134 G   D   L   G   F   F   S   K   G   Q   M   Q   F   E   E   A   A   F   N   L   H   V   G  150

730 GAA GTC AGT AAC ATA ATT GAA ACC AAT AGT GGT GTC CAT ATC CTC CAA AGA ACA GGA TAA ATCAAGATATTGGAGTTTGA  809
151 E   V   S   N   I   I   E   T   N   S   G   V   H   I   L   Q   R   T   G   *                      178

810 TGAAAAATGAAAAATAAATAGAGACAAGTTGTATAGATTGGTAACCAAAAAGCGATGGCTCACAAAAGTCGAAAACTGTGGAGAGAACATCTTACCAGG 909

910 TACACGGCGATTAAACTCTAATCGTCGATATTTATATAATCGGAACGTTTCCCGTCATTGGTTTTGTATATTTGGATCC  989
```

The CaESS1 gene of *Candida albicans*

FIG. 1A

Gene Knockout of CaESS1 in Candida albicans

Yeast Strain to Identify Inhibitors Specific for *Candida albicans* CaESS1

Screen for *hPIN1* Inhibitors

SEQUENCE LISTING

<160> NUMBER OF SEQ ID NOS: 8

<210> SEQ ID NO 1
<211> LENGTH: 989
<212> TYPE: DNA
<213> ORGANISM: Candida albicans

<400> SEQUENCE: 1

```
gatcaaccaa tagatgttgt tgctaaccaa gtcaaagacg cgttgaagac aagaggtatt      60
tagacacaca agcattagtc acttgaatag atatacagtt gagattcgtc ttgcaataga     120
tattaaggta gtgtacattt accaaaactt ctctcttttt ctatattctt catcaacaca     180
agattttcgt tgttgccttt tgttgtatta tttgtcatca gtttagcttg attcttttg     240 cagtagtata tcatcatggc atcgacatca acaggcttac cacctaattg gacgattaga     300
gtatccagat cccataacaa agagtatttc ttaaaccaat ctaccaatga gtcgtcttgg     360
gacccacctt atggcactga caaagaagta ttgaatgcat acattgcgaa gtttaaaaac     420
aatggttaca agccacttgt gaatgaggat ggccaggtta gagtttctca tttgttgatc     480
aagaacaatc aatcaagaaa acccaagtct tggaagtccc cagatggtat aagtagaact     540
agagacgaat ctatacagat attgaagaaa catttggaaa gaatattgag tggtgaggtt     600
aaactaagtg aattggcaaa taccgaaagt gattgcagct cacatgacag aggtggtgat     660
ttagggtttt ttagcaaagg acaaatgcaa ccaccattcg aagaagccgc attcaatttg     720
catgttggag aagtcagtaa cataattgaa accaatagtg gtgtccatat cctccaaaga     780
acaggataaa tcaagatatt ggagtttgat gaaaaatgaa aataaataga gacaagttgt     840
atagatttgg taaccaaaaa agcgatggct cacaaaagtc gaaaactgtg gagagaacat     900
cttaccaggt acacggcgat taaaactcta atcgtcgata tttatataat cggaacgttt     960
cccgtcattg gttttgtata tttggatcc                                      989
```

<210> SEQ ID NO 2
<211> LENGTH: 177
<212> TYPE: PRT
<213> ORGANISM: Candida albicans

<400> SEQUENCE: 2

Met Ala Ser Thr Ser Thr Gly Leu Pro Pro Asn Trp Thr Ile Arg Val
 1               5                  10                  15

Ser Arg Ser His Asn Lys Glu Tyr Phe Leu Asn Gln Ser Thr Asn Glu
            20                  25                  30

Ser Ser Trp Asp Pro Pro Tyr Gly Thr Asp Lys Glu Val Leu Asn Ala
        35                  40                  45

Tyr Ile Ala Lys Phe Lys Asn Asn Gly Tyr Lys Pro Leu Val Asn Glu
    50                  55                  60

Asp Gly Gln Val Arg Val Ser His Leu Leu Ile Lys Asn Asn Gln Ser
65                  70                  75                  80

Arg Lys Pro Lys Ser Trp Lys Ser Pro Asp Gly Ile Ser Arg Thr Arg
                85                  90                  95

Asp Glu Ser Ile Gln Ile Leu Lys Lys His Leu Glu Arg Ile Leu Ser
            100                 105                 110

Gly Glu Val Lys Leu Ser Glu Leu Ala Asn Thr Glu Ser Asp Cys Ser
        115                 120                 125

Ser His Asp Arg Gly Gly Asp Leu Gly Phe Phe Ser Lys Gly Gln Met
    130                 135                 140

Gln Pro Pro Phe Glu Glu Ala Ala Phe Asn Leu His Val Gly Glu Val
145                 150                 155                 160

Ser Asn Ile Ile Glu Thr Asn Ser Gly Val His Ile Leu Gln Arg Thr
                165                 170                 175

Gly

<210> SEQ ID NO 3
<211> LENGTH: 20
<212> TYPE: DNA
<213> ORGANISM: Candida albicans

<400> SEQUENCE: 3
ccagatggta taagtagaac                                               20

<210> SEQ ID NO 4
<211> LENGTH: 20
<212> TYPE: DNA
<213> ORGANISM: Candida albicans

<400> SEQUENCE: 4
atcaacggct acatccagaa                                               20

<210> SEQ ID NO 5
<211> LENGTH: 20
<212> TYPE: DNA
<213> ORGANISM: Candida albicans

<400> SEQUENCE: 5
gacgctacgg acgaactgaa                                               20

<210> SEQ ID NO 6
<211> LENGTH: 20
<212> TYPE: DNA
<213> ORGANISM: Candida albicans -continued

```
<400> SEQUENCE: 6
caatgacggg aaacgttccg                                               20

<210> SEQ ID NO 7
<211> LENGTH: 20
<212> TYPE: DNA
<213> ORGANISM: Candida albicans

<400> SEQUENCE: 7
gggagtgggg accccagggc                                               20

<210> SEQ ID NO 8
<211> LENGTH: 20
<212> TYPE: DNA
<213> ORGANISM: Candida albicans

<400> SEQUENCE: 8
gtcatctgga gaggaaaaga                                               20
```

CAESS1: A *CANDIDA ALBICANS* GENE, METHODS FOR MAKING AND USING, AND TARGETING IT OR ITS EXPRESSION PRODUCTS FOR ANTIFUNGAL APPLICATIONS

This application is a divisional of U.S. application Ser. No. 09/507,242, filed Feb. 18, 2000 now U.S. Pat. No. 6,537,753, issued Mar. 25, 2003.

STATEMENT OF GOVERNMENT INTEREST

Without any prejudice or admission, this invention may have been made with funding from the National Institutes of Health, HRI grant #815-3487, such that the U.S. Government may have certain rights.

FIELD OF THE INVENTION

The present invention relates to compositions and methods for diagnosing and/or detecting and/or preventing and/or treating *Candida albicans* or conditions or symptoms associated therewith, as well as to process and products for preparing such compositions and methods.

The present invention further relates to CaESS1, an important *Candida albicans* gene, e.g., nucleic acid molecules therefor, and/or fragments or portions thereof, expression products therefrom, e.g., the protein CaEss1 or fragments or portions thereof, methods for making and using the gene, portions thereof and expression products therefrom, and to targeting the gene or portions thereof and/or the expression products therefrom for antifungal applications.

The identification of the CaESS1 gene allows for identifying compounds or agents that specifically bind to and/or inhibit the gene, or portions thereof and/or expression products therefrom, and methods for preventing and/or treating *Candida albicans* and/or symptoms or conditions associated therewith, as well as generally for making and using such compounds or agents. Thus, the invention relates to antifungal preparations and/or compositions and methods for making and using them.

The CaEss1 amino acid sequence and the CaESS1 DNA or nucleic acid sequences can be used for diagnostic purposes. For instance, the nucleic acid sequences can be used to generate primers for diagnostic DNA, and the invention comprehends such primers. Primers are preferably derived from those parts of the CaESS1 gene which are least conserved among the ESS1/PIN1 family members. The gene or the primers can be used to detect if the gene is present in a sample or specimen and/or if the gene was expressed as RNA in a sample or specimen. Accordingly, the invention relates to compositions and methods for detecting and/or diagnosing *Candida albicans*.

The CaESS1 gene and portions thereof are useful for generating or expressing the CaEss1 protein and epitopic portions thereof (epitopic portions of the protein can be derived from, generated by, or expressed from those parts of the CaESS1 gene which are least conserved among the ESS1/PIN1 family members). The protein or portions thereof is useful for generating antibodies, such as monoclonal and/or polyclonal antibodies. These antibodies can be used for diagnostic purposes; and, the protein or portions thereof can be used for diagnostic purposes, e.g., the antibodies can be used to detect or determine, e.g., via binding, whether the proteins or portions thereof are present in a sample or specimen and the protein or portions thereof can be used to detect or determine, e.g., via binding, whether antibodies thereto are present in a sample or specimen. Further, the antibodies can be used to block CaEss1 activity. Accordingly, the invention relates to diagnostic compositions and methods, as well as therapeutic or preventive compositions and methods.

The invention further relates to methods for screening compounds for the ability to inhibit CaEss1 and/or PIN1. Compounds which selectively inhibit CaEss1 and do not inhibit PIN1 or do not inhibit PIN1 greatly are compounds useful in the prevention and/or treatment of *Candida albicans*. Compounds which inhibit PIN1 are useful in antiproliferative applications, e.g., as antineoplastic, anti-tumor or anticancer agents. Furthermore, the screening methods of the invention can be adapted and used for screening compounds which inhibit other fungal infection as fungus other than *Candida albicans* have ESS1 genes. Accordingly, the invention relates to methods for screening for inhibitors of CaEss1, PIN1 or other ESS1s, as well as to inhibitors of these enzymes.

Various documents are cited in the following text, or in a reference section preceding the claims. Each of the documents cited herein, and each of the references cited in each of those various documents, is hereby incorporated herein by reference. None of the documents cited in the following text is admitted to be prior art with respect to the present invention.

BACKGROUND OF THE INVENTION

*Candida albicans* is an asexual yeast species. *Candida albicans* is a major fungal pathogen of humans. It is can be found as a harmless commensal organism, inhabiting mucosal membranes and the digestive tract; a benign saprophyte. However, *Candida albicans*, can infect both internal organs and mucous membranes of the mouth, throat, and genital tract, and can cause a chronic infection; it can cause superficial infections, such as oral thrush, and can cause severe, often fatal, systemic infections, especially in immunocompromised patients.

There has been a growing number of cases of thrush and other diseases caused by *Candida albicans*; and, this can be attributed mainly to medical advances in antibiotic, steroid and immunosuppressive treatments, as well as to immunocompromising ailments such as HIV and AIDS. Indeed, surveillance of nosocomial blood stream infections (BSI) in the USA between April 1995 and June 1996 revealed that *Candida albicans* was the fourth leading cause of nosocomial BSI (Pfaller et al., "National surveillance of nosocomial blood stream infection due to *Candida albicans*: frequency of occurrence and antifungal susceptibility in the SCOPE Program," *Diagn Microbiol Infect Dis* 1998 May; 31(1):327–32). Accordingly, *Candida albicans*, and compositions and methods for detecting, diagnosing, preventing or treating *Candida albicans* are medically significant.

Thrush is characterized by creamy-white, curdlike patches on the tongue and other mucosal surfaces of the mouth. The disease is caused by an overgrowth of *Candida albicans*. Patients susceptible to thrush include immunocompromised individuals, e.g., adults whose immune systems have been weakened by antibiotics, steroids, immunosuppression treatments, AIDS, and the like, as well as infants, for instance if the mother had a vaginal yeast infection.

Painful, raw and bleeding areas result if the curdlike discharge is removed from patches of thrush. These superficial lesions may allow the yeast to spread to other areas of the body. *Candida albicans* can invade major organs, causing serious complications.

While thrush is typically treated with a topical agent, and there are oral and intravenous treatments for *Candida albicans* infections, chronically infected patients may require long term therapy with oral and/or intravenous therapy.

Moreover, strains of *Candida albicans* resistant to present treatments or therapies such as amphotericin B, fluconazole, itraconazole and other azole antifungals have been isolated (Mori et al., "Analysis by pulsed-field gel electrophoresis of *Candida albicans* that developed resistance during antifungal therapy," *Nippon Ishinkin Gakkai Zasshi* 1998;39(4): 229–33; Pfaller et al., supra; Rex et al., "A randomized trial comparing fluconazole with amphotericin B for the treatment of candidemia in patients without neutropenia," *N Engl J Med Nov* 17, 1994;331(20):1325–30). Indeed, in Rex et al., in certain individuals, treatment failed to clear infection from the bloodstream, and *Candida albicans* was infection commonly associated with the treatment failure.

Thus, there is a need for new treatments or therapies against *Candida albicans*.

Diagnosis of *Candida albicans* requires microscopic identification of the pseudomycelial (branching-arms) forms. There is likewise a need for new compositions and methods for diagnosing or detecting *Candida albicans*.

The ESS1 gene was originally discovered in *Saccharomyces cerevisiae*, by inventor Hanes working in the laboratory of Dr. Peter Shank and Dr. Keith Bostian (Hanes 1988). It was discovered in a search for cell growth control genes. By gene disruption techniques, ESS1 was shown to be essential for yeast cell growth, hence the name (Essential) (Hanes et al. 1989). ESS1 genes are highly conserved. Homologs of the ESS1 gene have been found in *Drosophila*, humans and several other organisms. The fly gene (called dodo) and the human gene (called PIN1) encode proteins that are 45% identical to the yeast Ess1 protein (Maleszka et al. 1996; Lu et al. 1996).

U.S. Pat. No. 5,952,467 to Hunter et al. relates to the identification and characterization of Pin1, a protein of mammalian origin that associates with NIMA protein kinase. It was determined that overexpression of Pin1 activity induces a specific G2 arrest and delays NIMA-induced mitosis, while depletion of Pin1 triggers mitotic arrest and nuclear fragmentation. The specification provides for a method of controlling the growth of a cell by contacting the cell with a composition which modulates the Pin1 activity. The corresponding nucleic acid sequence encoding Pin1 is identified in U.S. Pat. No. 5,972,697 to Hunter et al.

However, prior to the present invention, the *Candida albicans* ESS1 or CaESS1 gene had not been isolated, or sequenced; or disclosed or suggested, nor had corresponding amino acid sequences from the gene been disclosed or suggested. Likewise, fragments or portions of the gene and protein had not been disclosed or suggested. Also, diagnostic, prophylactic, therapeutic, or similar compositions and methods involving the gene and/or the protein and/or fragments of the gene and/or fragments of the protein, had not been taught or suggested.

In view of the significance of *Candida albicans*, and the need for new therapies, treatments, means for prevention, and means for diagnosing or detecting *Candida albicans*, providing the CaESS1 gene, portions thereof, amino acid sequences from the gene, fragments or portions of the protein, and diagnostic, prophylactic, therapeutic, or similar compositions and methods involving the gene and/or the protein and/or fragments of the gene and/or fragments of the protein, are significant advances in the art, addressing problems in the art.

OBJECTS AND SUMMARY OF THE INVENTION

An object of the invention can include providing any or all of: the CaESS1 gene, portions thereof, amino acid sequences from the gene, fragments or portions of the protein, and diagnostic, prophylactic, therapeutic, or similar compositions and methods involving the gene and/or the protein and/or fragments of the gene and/or fragments of the protein.

Accordingly, the present invention provides an isolated and/or purified nucleic acid molecule encoding CaEss1, e.g., CaESS1; for instance, an isolated and/or purified nucleic acid molecule comprising a nucleotide sequence encoding CaEss1 as set forth in FIG. 1 (SEQ ID NO: 1).

The present invention also provides an isolated and/or purified nucleic acid molecule which is a primer for an isolated and/or purified nucleic acid molecule encoding CaEss1, e.g., CaESS1, for instance, a primer for an isolated and/or purified nucleic acid molecule comprising a nucleotide sequence encoding CaEss1 as set forth in FIG. 1. Such a primer can be OW-216 or OW-221 disclosed below (SEQ ID NOS: 3, 6).

The present invention also provides an isolated and/or purified CaEss1 protein; for instance, such a protein from expression of any or all of the foregoing nucleic acid molecules, or as shown in FIG. 1 (SEQ ID NO:2).

The invention further provides nucleic acid molecules and amino acid molecules having at least 70%, e.g., at least 75%, such as at least 80%, e.g., at least 85%, preferably at least 90%, more preferably at least 95% such as at least 97% homology, identity or similarity to such molecules disclosed herein.

The invention further provides diagnostic compositions and methods involving the nucleic acid molecules, as well as the amino acid molecules or antibodies generated therefrom.

Thus, the invention further provides methods for determining the presence of *Candida albicans* in a sample; for instance, by detecting the presence in the sample of CaESS1 e.g., by diagnostic PCR using a primer or probe specific for CaESS1; or, by detecting CaEss1 by contacting the sample with an antibody specific for CaEss1 and detecting binding of the antibody; or by detecting antibodies to CaEss1 by contacting the sample with an inventive amino acid molecule and detecting binding thereof to an antibody in the sample.

The invention further provides therapeutic or preventive compositions, e.g., compositions useful for treating or preventing a fungal infection such as a *Candida albicans* infection or for antiproliferative effect, e.g., antineoplastic, anti-tumor or anti-cancer effect, as well as to methods for treating or preventing such fungal infections or cell proliferation.

A CaEss1 inhibitor can be a compound which selectively inhibits growth of *S. cerevisiae* not containing an endogenous ESS1 gene but rather CaEss1 and uninduced PIN1 (e.g., on a glucose medium, see FIGS. 2, 3) and/or preferably does not inhibit or significantly inhibit induced PIN1, e.g., does not inhibit or significantly inhibit *S. cerevisiae* not containing an endogenous ESS1 gene but rather induced PIN1 (see FIG. 3). An anti-CaEss1 antibody or an antibody against an epitopic region of CaEss1 can also be an inhibitor of CaEss1 by virtue of the antibody being able to bind to CaEss1. Compositions which indeed inhibit PIN1 are nonetheless useful as antiproliferatives, e.g., antineoplastics, antitumor agents or anti-cancer agents.

The invention comprehends methods for preventing or treating *Candida albicans* or cancer by administering the inventive compositions.

Further still, the invention provides methods for screening compounds for inhibiting *Candida albicans*, as well as other fungal infectious agents, and human cell growth. The screening method entails plating yeast transformed to express a fungal ESS1 gene such as CaESS1 alone or with PIN1, and contacting those yeast with a potential inhibitory compound, whereby compounds specifically inhibit yeast cell growth when CaEss1 is expressed, but not when PIN1 is expressed. Such compounds are specific inhibitors of ESS1 such as CaEss1, but not PIN1.

The invention yet further still entails a method for screening for antiproliferative compounds, e.g., anti-tumor, anti-cancer or antineoplastic agents, comprising plating yeast transformed to express low or high levels of PIN1 (e.g., on glucose/galactose and glucose media) and determining compounds which selectively inhibit growth of yeast expressing low levels of PIN1, e.g., on the glucose/galactose medium, but not growth of yeast expressing high levels of PIN1, e.g., on the galactose medium.

These and other embodiments are disclosed or are obvious from and encompassed by, the following Detailed Description.

BRIEF DESCRIPTION OF FIGURES

The following Detailed Description, given by way of example, but not intended to limit the invention to specific embodiments described, may be understood in conjunction with the accompanying Figures, incorporated herein by reference, in which:

FIG. 1A shows the complete nucleotide sequence of the CaESS1 gene from *Candida albicans* and its predicted translation product (the CaESS1-encoded protein (CaEss1) is 177 amino acids long and has a predicted molecular weight of 19.8 Kd; it is 42% identical to the ESS1 protein of *Saccharomyces cerevisiae*) (SEQ ID NOS: 1, 2);

DETAILED DESCRIPTION

Figure 1B:
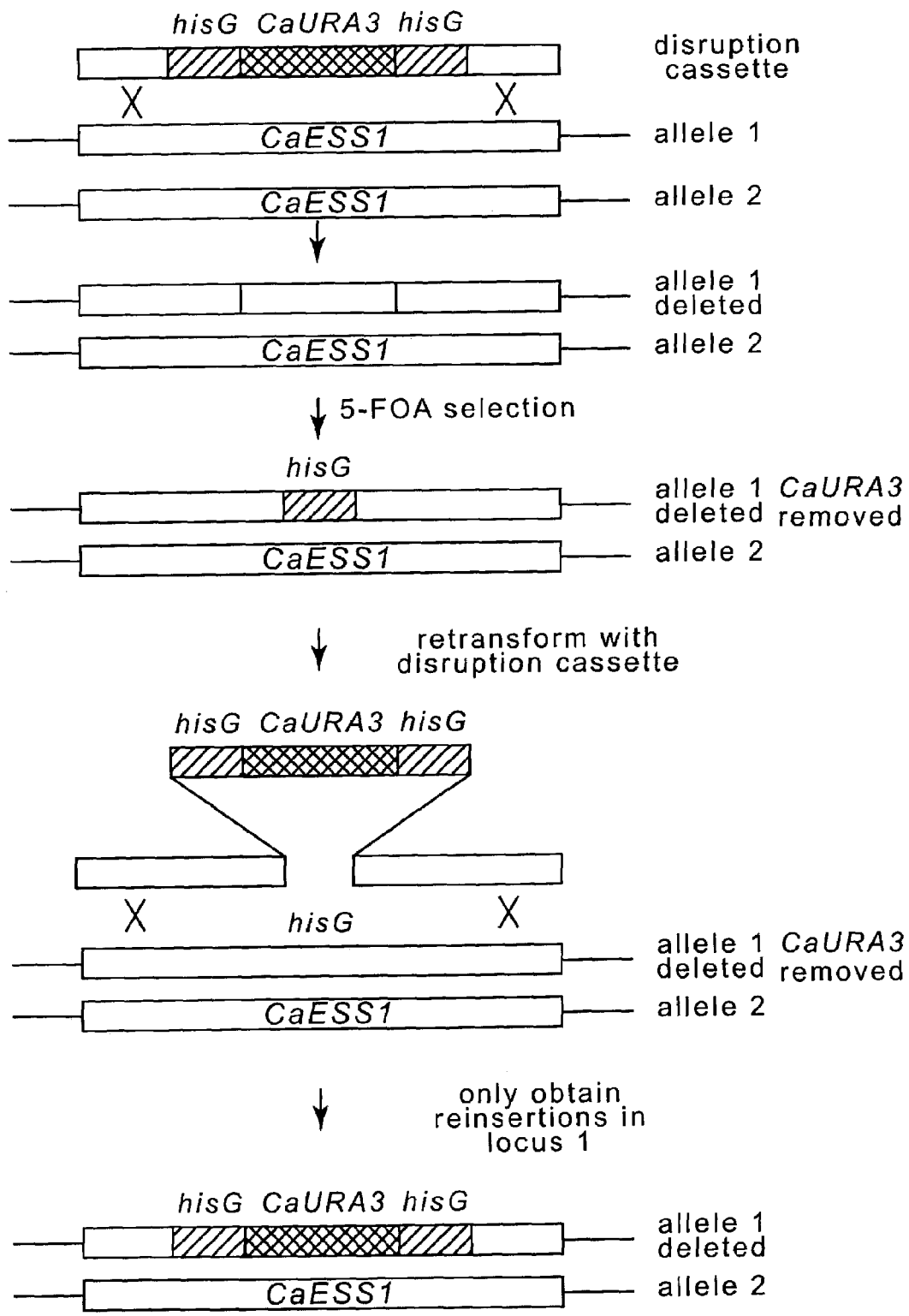
FIG. 1B shows the strategy used to delete CaESS1 from *C. albicans* and Table 1 summarizes the results obtained, which are consistent with CaESS1 being essential in this organism.

Peptidyl-prolyl cis/trans isomerases (PP1ases) fall broadly into three families: Cyclophilins, FKBPs and Parvulins. Parvulins, a recently discovered family, are distinct from the cyclophilins and FKBPs in both structure and substrate specificity. The Ess1 protein from *Saccharomyces cerevisiae* is a member of the parvulin-family of PPIases and is the only PPIase essential for growth in this organism. Depletion of Ess1 causes mitotic arrest and nuclear fragmentation. Homologs of the ESS1 gene have been found in many organisms, including humans (PIN1), *Drosophila* (dodo), *Aspergillus, Schizosaccharomyces* and *Neurospora*.

To explore the role of Ess1 in the biology and virulence of *Candida albicans*, Applicants sought to isolate a *C. albicans* homolog. Given the essential role of Ess1 in *S. cerevisiae*, and its high degree of structural and functional conservation, Applicants used temperature-sensitive ess1 mutants (ess1$^{ts}$) in *S. cerevisiae*. A multicopy *C. albicans* genomic library was used to complement the growth defect of an ess1$^{ts}$ mutant strain at the restrictive temperature (37° C.).

Applicants obtained 5 clones from a total of 2.0×10$^6$ transformants whose complementing activity was plasmid-linked. Three of the clones carried an extragenic suppressor. The other two carried an identical 8.5 kb DNA insert. Within the insert, a gene was identified encoding a 177 aa protein that is 42% identical to Ess1. Applicants call this gene CaESS1 (see FIG. 1).

A 1 kb subclone carrying only this gene was shown to complement several different ess1$^{ts}$ alleles in *S. cerevisiae*. Gene knockout experiments can show CaESS1 is an important gene in *C. albicans* and mutations in CaESS1 affect virulence in animal models.

More generally, herein Applicants provide the discovery of a gene from an important human pathogenic fungus, *Candida albicans*, that can serve as a useful antifungal drug target. This gene, called CaESS1, is functional in the common laboratory yeast, *Saccharomyces cerevisiae*, that has been used extensively for high-throughput screening. The invention comprehends inhibitors of CaESS1 or of its expressed protein CaEss1, e.g., compounds or agents which bind to either the nucleic acid molecule or the expressed protein; and, this description provides a means using *Saccharomyces cerevisiae* to carry out large screens for such inhibitors so that in view of this disclosure and the knowledge in the art, no undue experimentation is required to identify compounds or agents which so act as inhibitors. Such inhibitors can then be developed into new broad-spectrum drugs to treat patients with *Candida albicans* infections, and potentially other life-threatening fungal infections.

The ESS1 gene was originally discovered in *Saccharomyces cerevisiae* (Hanes 1988). It was discovered in a search for cell growth control genes. By gene disruption techniques, ESS1 was shown to be essential for yeast cell growth, hence the name (Essential) (Hanes et al. 1989).

ESS1 genes are highly conserved. Homologs of the ESS1 gene have been found in *Drosophila*, humans and several other organisms. The fly gene (called dodo) and the human gene (called PIN1) encode proteins that are 45% identical to the yeast Ess1 protein (Maleszka et al. 1996; Lu et al. 1996). When introduced into ESS1 knockout strains of yeast, both the fly and human genes rescue the lethal phenotype. These results demonstrate that these ESS1 homologs carry out similar functions by acting on common targets within cells of the respective organism. Given that ESS1 is highly conserved, it is likely to be present in many different pathogenic fungi, and based on its role in budding yeast, these ESS1 homologs are likely to be essential.

Indeed, "gene knockout" results obtained by the applicants strongly suggest that the CaESS1 gene is essential for growth in *C. albicans* just as the ESS1 gene is essential in *S. cerevisiae*. *C. albicans* is a diploid organism and therefore should have two alleles of CaESS1. Experiments done by the applicants show that it is possible to delete one of the two alleles of CaESS1 in *C. albicans* (FIG. 1B). This was done by the standard method of homologous recombination as described by Fonzi and Irwin (1993). However, the applicants have not been able to delete the second and remaining allele of CaESS1 in *C. albicans* indicating that at least one allele is required for growth under experimental conditions.

ESS1 plays an essential role in mitosis. Using recombinant DNA techniques and yeast genetics to engineer strains in which ESS1 or PIN1 gene expression is controlled by changing the carbon source, ESS1 is shown to be required for cells to complete mitosis, a critical stage of the cell division cycle in which cells separate their chromosomes and organelles to form two complete cells (Lu et al., 1996). These results were confirmed using temperature-sensitive ESS1 mutants. How exactly ESS1 controls mitosis is not yet known, although work with the human homolog (PIN1) suggests it might bind and/or regulate mitotic phosphoproteins that are targets of the p34$^{cdc2}$ G2/M kinase (Shen et al. 1998). Work done with the *S. cerevisiae* ESS1 by the applicants and others suggest that the ESS1 protein is also important for transcription, perhaps by interacting with RNA polymerase II and other factors required for transcription (Morris et al., 1999; Wu et al., 2000; Arevalo-Rodriguez et al., 2000).

Clues to how ESS1 family members might work: Some clues are provided by the discovery that ESS1 proteins contains two recognizable domains.

The first is a WW domain, identified in a number of seemingly unrelated proteins from different organisms, that has been shown to mediate protein-protein interactions important for intracellular signaling (Sudol 1996). Its is therefore likely, that ESS1 proteins contact other proteins via the WW domain.

The second domain is a peptidylprolyl cis-trans isomerase (PP1ase) domain that is found in proteins that catalyze the isomerization of prolyl-containing peptides (Hemenway et al. 1993). PPlase proteins are thought to be important for protein folding, but are more widely known because they mediate the effects of immunosuppressive drugs like cyclosporin and FK506. The presence of a PPlase domain suggests that Ess1 may control the activity of other proteins by changing their conformational states by isomerization.

Isolation of the *Candida albicans* homolog of ESS1: To isolate a *Candida albicans* homolog of ESS 1, Applicants isolated temperature sensitive mutations in the budding yeast ESSI gene. At the time of this invention, these were the only ts-conditional mutants available for an ESS1 family member in any organism. A temperature sensitive mutant is also reported by Hani et al., "Mutations in a peptidylprolyl-cis/trans-isomerase gene lead to a defect in 3'-end formation of a pre-mRNA in *Saccharomyces cerevisiae*", J. Biol. Chem., January 1999; 274(1):108–16. Yeast strains carrying these mutations (ESS1$^{ts}$) grow normally at the permissive temperature (30° C.), but do not grow at the restrictive temperature (37° C.). To clone the *Candida albicans* ESS1 gene, a high-copy plasmid library containing *Candida albicans* genomic DNA was transformed into one of the ess1$^{ts}$ strains and colonies were selected for growth at the restrictive temperature. Among the colonies that grew, two carried an identical 8.5 kb DNA insert. Within this DNA insert, a gene was identified whose predicted protein product is 42% identical at the amino acid level to the Ess1 protein (FIG. 1). Further complementation experiments showed that this gene is necessary and sufficient to rescue the lethal phenotype of an ess1$^{ts}$ mutant. The gene was named CaESS1 (*Candida albicans* ESS1). Of course, with the disclosure herein of the nucleic acid sequence for CaESS1 as well as for primers for it, a preferred means for isolating CaESS1 is by amplification (e.g., PCR) of the gene using the nucleic acid sequence for CaESS1 or primers derived therefrom, such as primers disclosed herein.

CaESS1 as a Drug Target: The protein encoded by CaESS1, namely CaEss1, is an excellent target for antifungal drugs. The Ess1 protein is a highly conserved, essential PPlase whose activity is likely to be required for cell growth in a wide variety of pathogenic fungi. As mentioned previously, gene knockout experiments by the applicants suggest that CaESS1 is essential for growth in *C. albicans*, and work with other fungi, such as *Aspergillus nidulans*, shows that the ESS1 gene homolog is essential for growth in that organism (Dr. Anthony Means, Duke University, personal communication). In budding yeast, loss of Ess1 function causes mitotic arrest and nuclear fragmentation. This phenotype is not reversible, i.e. it is cytotoxic, not cytostatic. PPlases have been intensely studied as targets of immunosuppressive drugs but heretofore have not been fully explored as targets of antifungal drugs (see Hemenway et al.

1993; Georgopapadakou et al. 1994). Compounds such as rapamycin inhibit the growth of *Saccharomyces cerevisiae* by binding to a class of PPlases known as FKBPs. However, in yeast, none of the FKBP-class of PPlases nor the cyclophilin-class of PPlases are essential for growth (Dolinski et al. 1997). Therefore, spontaneous mutations that abolish production of FKBP (or cyclophilin) remain viable, and are resistant to rapamycin (or cyclosporin A). This mechanism of resistance can pose a major clinical problem. In contrast, Ess1 protein is a parvulin-class PPlase (Rudd et al. 1995) and is absolutely required for growth in *Saccharomyces cerevisiae*; it is the only known PPlase that exhibits this property. Mutations that abolish production of Ess1 protein would be lethal; therefore, resistance by this mechanism would not occur. Known inhibitors of the FKBPs and cyclophilins (e.g. FK506, cyclosporin A) are not active against parvulin-class PPlases (Rudd et al. 1995). There are no specific inhibitors known to date. Finally, given the strong conservation of Ess1, it is likely that agents that inhibit *Candida albicans* Ess1 will also inhibit Ess1 homologs from other pathogenic yeasts such as *Cryptococcus neoformans* or *Aspergillus fumigatus*.

One possible concern is that anti-CaESS1 or anti-CaEss1 drugs might also interfere with function of the human counterpart, PIN1 or PIN1. However, the disclosure herein provides screening methods to overcome this possible concern. Furthermore, based on work in *Drosophila* (Maleszka et al.) and in mice (Fujimori et al., 1999) it is almost certain that PIN1 is not essential in humans, although there may be PIN1-related genes which have functional overlap with PIN1. Nonetheless, to avoid possible toxicity, Applicants screening methods aim to isolate compounds that preferentially target the fungal form of the enzyme over the human form. To do this *Saccharomyces cerevisiae* strains are engineered so they express, in a conditional manner both *Candida albicans* CaESS1 and human PIN1. Using these strains, it is possible to identify compounds that preferentially inhibit the fungal form of the enzyme. In addition, by using variant screens, it is possible to identify compounds that inhibit the human form of the enzyme, and these might usefully be developed as antiproliferative (anti-cancer) agents.

Thus, the present invention provides CaESS1, an essential *Candida albicans* gene, e.g., nucleic acid molecules therefor, and/or fragments or portions thereof, expression products therefrom, e.g., the protein CaEss1 or fragments or portions thereof, methods for making and using the gene, portions thereof and expression products therefrom, and to targeting the gene or portions thereof and/or the expression products therefrom for antifungal applications.

Inventive nucleic acid molecules include nucleic acid molecules having at least 70% identity or homology or similarity with CaESS1 or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11–17, 1988) and available at NCBI. Using this method, the CAESS1 gene is 53.7% identical to *S. cerevisiae* ESS1 gene, and the CaESS1 gene is 50.5% identical to human ESS1 (PIN1) gene. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGT-CAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in CaESS1 which are unique to CaESS1 or which are in CaESS1 and are least conserved among the ESS1/PIN1 family. As to PCR or hybridization primers or probes and optimal lengths therefor, reference is also made to Kajimura et al., GATA 7(4):71–79 (1990).

RNA sequences within the scope of the invention are derived from the DNA sequences, by thymidine (T) in the DNA sequence being considered equal to uracil (U) in RNA sequences.

Inventive amino acid molecules include amino acid molecules having at least 70% identity or homology or similarity with CaEss1 or portions thereof derived from the sequence provided herein such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. Amino acid sequence similarity or identity or homology can be determined using the BlastP program (Altschul et al., Nucl. Acids Res. 25, 3389–3402) and available at NCBI. By this program, CaEss1 protein is 42% identical to *S. cerevisiae* Ess1 protein, and CaEss1 protein is 43% identical to human Ess1 (Pin1) protein. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. The following references provide algorithms for comparing the relative identity of amino acid residues of two proteins: Needleman S B and Wunsch C D, "A general method applicable to the search for similarities in the amino acid sequences of two proteins," *J. Mol. Biol.* 48:444–453 (1970); Smith T F and Waterman M S, "Comparison of Bio-sequences," *Advances in Applied Mathematics* 2:482–489 (1981); Smith T F, Waterman M S and Sadler J R, "Statistical characterization of nucleic acid sequence functional domains," *Nucleic Acids Res.,* 11:2205–2220 (1983); Feng D F and Dolittle R F, "Progressive sequence alignment as a prerequisite to correct phylogenetic trees," *J. of Molec. Evol.,* 25:351–360 (1987); Higgins D G and Sharp P M, "Fast and sensitive multiple sequence alignment on a microcomputer," *CABIOS,* 5: 151–153 (1989); Thompson J D, Higgins D G and Gibson T J, "ClusterW: improving the sensitivity of progressive multiple sequence alignment through sequence weighing, positions-specific gap penalties and weight matrix choice, *Nucleic Acid Res.,* 22:4673–480 (1994); and, Devereux J, Haeberlie P and Smithies 0, "A comprehensive set of sequence analysis program for the VAX," *Nucl. Acids Res.,* 12: 387–395 (1984).

Like probes or primers, amino acids of the invention which are not full-length CaEss1 as depicted in FIG. 1 can be any stretch of at least 8, preferably at least 10, more preferably at least 12, 13, 14, or 15, such as at least 20, e.g., at least 23 or 25, for instance at least 27 or 30 amino acids in CaEss1 which are unique to CaEss1 or which are in CaEss1 and are least conserved among the ESS1/PIN1 family. Alternatively or additionally, the amino acids of the invention which are not full length CaEss1 can be an epitopic region of CaEss1; for instance, to generate antibodies specific to CaEss1. One skilled in the art can determine an epitopic region of CaEss1 or an epitope of interest in CaEss1, without undue experimentation, from the disclosure herein and the knowledge in the art; see, e.g., WO 98/40500 regarding general information for determining an epitope of interest or an epitopic region of a protein.

The CaESS1 gene or portions thereof can be expressed in yeast expression systems (see Examples or U.S. Pat. No. 4,752,473), or other vectors. Methods for making and/or using such other vectors (or recombinants) for expression be by or analogous to the methods disclosed in: U.S. Pat. Nos. 4,603,112, 4,769,330, 5,174,993, 5,505,941, 5,338,683, 5,494,807, 4,722,848, WO 94/16716, WO 96/39491, Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, Dec., 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirus-based expression vectors: Strategies and applications," PNAS USA 93:11371–11377, October 1996, Kitson et al., J. Virol. 65, 3068–3075, 1991; U.S. Pat. Nos. 5,591,439, 5,552,143 (recombinant adenovirus), Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259: 1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos. 5,591,639, 5,589,466, and 5,580,859 relating to DNA expression vectors, inter alia. See also WO 98/33510; Ju et al., Diabetologia, 41:736–739, 1998 (lentiviral expression system); Sanford et al., U.S. Pat. No. 4,945,050; Fischbach et al. (Intracel), WO 90/01543; Robinson et al., seminars in IMMUNOLOGY, vol. 9, pp.271–283 (1997) (DNA vector systems); Szoka et al., U.S. Pat. No. 4,394,448 (method of inserting DNA into living cells); and McCormick et al., U.S. Pat. No. 5,677,178 (use of cytopathic viruses), as well as other documents cited herein.

The expression product from the CaESS1 gene or portions thereof can be useful for generating antibodies such as monoclonal or polyclonal antibodies which are useful for diagnostic purposes or to block CaEss1 enzyme activity.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Thus, products expressed from CaESS1 or portions thereof are useful in immunoadsorption chromatography, as well as for generating antibodies for diagnostic purposes. Furthermore, the expression products can be used in assays for detecting the presence of anti-CaEss1 antibodies.

For instance, the antibodies or expressed products can be used in assays analogous to those disclosed in U.S. Pat. Nos. 5,591,645, 4,861,711, 5,861,319, 5,858,804, and 5,863,720, as well as in WO 86/04683, EP 154 749, WO 86/03839, and EP 186 799.

For instance, one can assay for *Candida albicans* by i) contacting, e.g., in a single test vessel, first and second capture agents respectively for first and second serological markers of *Candida albicans* infection, with a sample e.g., derived from a patient suspected to suffer therefrom (said sample suspected to contain said first and second markers, so as to permit any first and second disease markers in said sample to bind to said capture agents); ii) then contacting said capture agents with first and second labelled revealing agents bearing first and second labels respectively such that said first revealing agent gives a first signal corresponding to the amount of said first marker in said sample and said second revealing agent gives a second signal combinable with said first signal and corresponding to the amount of said second marker in said sample; iii) combining said first and second signals into a third signal, iv) detecting said third signal, and v) correlating the presence or absence of a *Candida albicans* infection in said patient with the strength of the third signal, wherein the strength of said first signal increases monotonically with increasing concentration of said first marker in said sample and the strength of said second signal decreases monotonically with increasing concentration of said second marker in said sample.

The sample can be blood. The first marker can be an antibody against CaEss1 or a fragment thereof expressed from CaESS1 or a fragment thereof; or the first capture agent could be CaEss1 or a fragment thereof, e.g., expressed from CaESS1 or a fragment thereof. The first revealing agent can be labeled CaEss1 or a fragment thereof, e.g., expressed from CaESS1 or a fragment thereof. The second revealing agent can be a labelled antibody against CaEss1 or a fragment thereof, e.g., CaEss1 or a fragment thereof from expression of CaESS1 or a fragment thereof. The first and second capture agents can be bound to solid supports, e.g., the same solid support, such as a well of a microtitre plate. The first and second revealing agents can bear the same label, e.g., a radioisotope such as $^{125}$I, an enzyme such as horseradish peroxidase, or fluorescent labels.

Thus, the nucleic acid molecules of the invention can be used to express inventive amino acids and amino acid molecules of the invention can be used in diagnostic applications involving antibody-binding, without undue experimentation, from the knowledge in the art and this disclosure.

The CaESS1 DNA or inventive nucleic acid sequences can be used for diagnostic purposes. For instance, the nucleic acid sequences can be used to generate primers for diagnostic DNA, and the invention comprehends such primers. Primers are preferably derived from those parts of the CaESS1 gene which are least conserved among the ESS1/PIN1 family members. The gene or the primers can be used to detect if the gene is present in a sample or specimen and/or if the gene was expressed as RNA in a sample or specimen.

Accordingly, the inventive nucleotides can be used as probes to ascertain the presence of *Candida albicans* DNA in samples, as well as in the generation of PCR primers for replicating or cloning *Candida albicans* DNA. Methods for using DNA as probes or for preparing PCR primers are known in the art. In other words, the CaESS1 gene or portions thereof are useful for generating primers for diagnostic PCR.

In diagnostic PCR, it is preferred that the primers bind specifically to CaESS1, i.e., specific hybridization is preferred. One way to ensure this is to select primers from the CaESS1 gene sequence that are least conserved among ESS1/PIN1 family members.

The term "specific hybridization" will be understood to mean that the nucleic acid probes of the invention are capable of stable, double-stranded hybridization to *Candida albicans*-derived DNA or RNA under conditions of high stringency, as the term "high stringency" would be understood by those with skill in the art (see, for example, Sambrook et al., 1989, Molecular Cloning: A Laboratory Manual, Cold Spring Harbor Laboratory Press, Cold Spring Harbor, N.Y. and Hames and Higgins, eds., 1985, Nucleic Acid Hybridization, IRL Press, Oxford, U.K.). Hybridization will be understood to be accomplished using well-established techniques, including but not limited to Southern blot hybridization, Northern blot hybridization, in situ hybridization and, most preferably, Southern hybridization to PCR-amplified DNA fragments.

The nucleic acid hybridization probe of the invention may be obtained by use of the polymerase chain reaction (PCR) procedure, using appropriate pairs of PCR oligonucleotide primers as provided herein or derived from the CaESS1 gene sequence provided herein. See U.S. Pat. Nos. 4,683,195 to Mullis et al. and 4,683,202 to Mullis.

The invention provides oligonucleotides for in vitro amplification using any of a variety of amplification protocols known in the art. Preferably, the invention provides oligonucleotides for performing polymerase chain reaction (PCR). See U.S. Pat. No. 4,683,195 to Mullis et al. and U.S. Pat. No. 4,683,202 to Mullis.

The invention will thus be understood to provide oligonucleotides, specifically, pairs of oligonucleotides, for use as primers for the in vitro amplification of *Candida albicans* DNA samples and fragments thereof. In the practice of this invention, the pairs of oligonucleotides herein provided will be understood to comprise two oligonucleotides, comprising from about 8 to about 30 nucleotide residues apiece, said oligonucleotides specifically hybridizing to sequences flanking a nucleic acid to be amplified, wherein the oligonucleotides hybridize to different and opposite strands of the DNA target. The oligonucleotides of the invention are preferably derived from the nucleic acid primers discussed below or from the CaESS1 gene disclosed herein. As used in the practice of this invention, the term "derived from" is intended to encompass the development of such oligonucleotides from the nucleic acid sequence of the CaEss1 gene or the primers herein disclosed, from which a multiplicity of alternative and variant oligonucleotides can be prepared. In particular, the invention provides oligonucleotides having a sequence that is substantially complementary to the corresponding sequence of the nucleic acid hybridization probe. As used herein, the term "substantially corresponding to" is intended to encompass oligonucleotides comprising sequence additions, deletions and mismatches, wherein certain nucleotide residues of the oligonucleotide sequence are not optimally complementary (e.g., A-C or G-T) or are non-complementary (e.g., A-G or T-C) to the corresponding sequence of the nucleic acid hybridization probe, provided that such oligonucleotides retain the capacity to specifically amplify CaESS1.

Nucleic acids, e.g., CaESS1, and oligonucleotides therefrom, such as primers disclosed herein and derivable from the CaESS1 sequence of the present invention (e.g., portions of the disclosed CaESS1 which are about 8 to 30 or more nucleotides in length and bind with sufficient specificity to CaESS1 are useful as diagnostic tools for detecting the existence of a *Candida albicans* infection or the presence of *Candida albicans*. Such diagnostic reagents comprise nucleic acid hybridization probes of the invention and encompass paired oligonucleotide PCR primers, as described above.

Methods provided by the invention include blot hybridization, in situ hybridization and in vitro amplification techniques for detecting the presence of *Candida albicans* in a sample such as a biological sample. Appropriate biological samples advantageously screened using the methods described herein include blood, serum, saliva and other body fluids, and other potential sources of infection.

In the detection methods of the invention, production of a specific DNA fragment produced by in vitro amplification of a template DNA sample is detected by agarose gel electrophoresis, ethidium bromide staining and ultraviolet transillumination of ethidium bromide stained gels, performed using conventional techniques (Sambrook et al., supra), or detection by sequence detection systems using fluorogenic or other labeled probes that rely on automatic or automated detection instrumentation. In instances where a greater degree of specificity is required, hybridization of such agarose gels probed with a detectably-labeled nucleic acid hybridization probe of the invention is performed using standard techniques (Sambrook et al., supra). In each of these embodiments of the methods of the invention, a sufficient amount of a specific PCR-amplified DNA fragment is produced to be readily detected. For the purposes of this invention, the term "a sufficient amount of a specific PCR-amplified DNA fragment" is defined as that amount required to be detected, either by visualization of ethidium bromide-stained agarose gels or autoradiographic or other development of a blot hybridized with a detectably-labeled probe.

It will be understood that a sufficient quantity of a specific PCR amplified DNA fragment is prepared in PCR amplification reactions by performing a number of cycles required to produce said sufficient amount of the specific DNA fragment. The number of cycles in each PCR required to produce said sufficient amount of a specific DNA fragment will be understood to depend on the oligonucleotide primers, buffers, salts and other reaction components, the amount of template DNA and the PCR cycling times and temperatures. It will also be understood that the optimization of these parameters are within the skill of the worker of ordinary skill to achieve with no more than routine experimentation.

Detectably-labeled probes as provided by the invention are labeled with biotin, a radioisotope (including $^3H$, $^{14}C$, $^{35}S$ and $^{32}P$), a fluorescent label (including fluorescein isothiocyanate), and an antigenic label. The detectable label is incorporated into the probe during synthetic preparation of the probe, whereby the probe is alternatively end-labeled or labeled by the incorporation of labeled nucleotides into the synthesized probe.

The invention also provides a PCR-based method for preparing a nucleic acid hybridization probe of the invention. In these embodiments, template DNA comprises a recombinant genetic construct of the invention. A detectably-labeled nucleic acid hybridization probe is prepared by performing PCR amplification using a pair of oligonucleotide primers specific for sequences flanking the position of the nucleic acid insert. Detectable label is incorporated into the nucleic acid hybridization probe by direct end-labeling of PCR primers or incorporation of detectably-labeled nucleotide triphosphates into the probe nucleic acid. PCR comprising the methods of the invention is performed in a reaction mixture comprising an amount, typically between <10 ng–200 ng template nucleic acid; 50–100 pmoles each oligonucleotide primer; 1–1.25 mM each deoxynucleotide triphosphate; a buffer solution appropriate for the polymerase used to catalyze the amplification reaction; and 0.5–2 Units of a polymerase, most preferably a thermostable polymerase (e.g., Taq polymerase or Tth polymerase).

The invention thus provides diagnostic assays for the specific detection of Candida albicans. These diagnostic assays include nucleic acid hybridization assays, using the nucleic acids of the invention or specifically-hybridizing fragments thereof, for sensitive detection of fungal genomic DNA and/or RNA. Such assays include various blot assays, such as Southern blots, Northern blots, dot blots, slot blots and the like, as well as in vitro amplification assays, such as the polymerase chain reaction assay (PCR), reverse transcription-polymerase chain reaction assay (RT-PCR), ligase chain reaction assay (LCR), and others known to those skilled in the art. Specific restriction endonuclease digestion of diagnostic fragments detected using any of the methods of the invention, analogous to restriction fragment linked polymorphism assays (RFLP) are also within the scope of this invention.

Accordingly, the invention relates to compositions and methods for detecting and/or diagnosing Candida albicans.

Moreover, the identification of the CaESS1 gene allows for identifying compounds or agents that specifically bind to and/or inhibit the gene, or portions thereof and/or expression products therefrom, and methods for preventing and/or treating Candida albicans and/or symptoms or conditions associated therewith, as well as generally for making and using such compounds or agents. Thus, the invention relates to antifungal preparations and/or compositions and methods for making and using them.

As discussed herein, the CaESS1 gene and portions thereof are useful for generating or expressing the CaEss1 protein and epitopic portions thereof (epitopic portions of the protein can be derived from, generated by, or expressed from those parts of the CaESS1 gene which are least conserved among the ESS1/PIN1 family members). The protein or portions thereof is useful for generating antibodies, such as monoclonal and/or polyclonal antibodies. In addition to using these antibodies for diagnostic purposes, the antibodies can be used to block CaEss1 activity.

Figure 3:
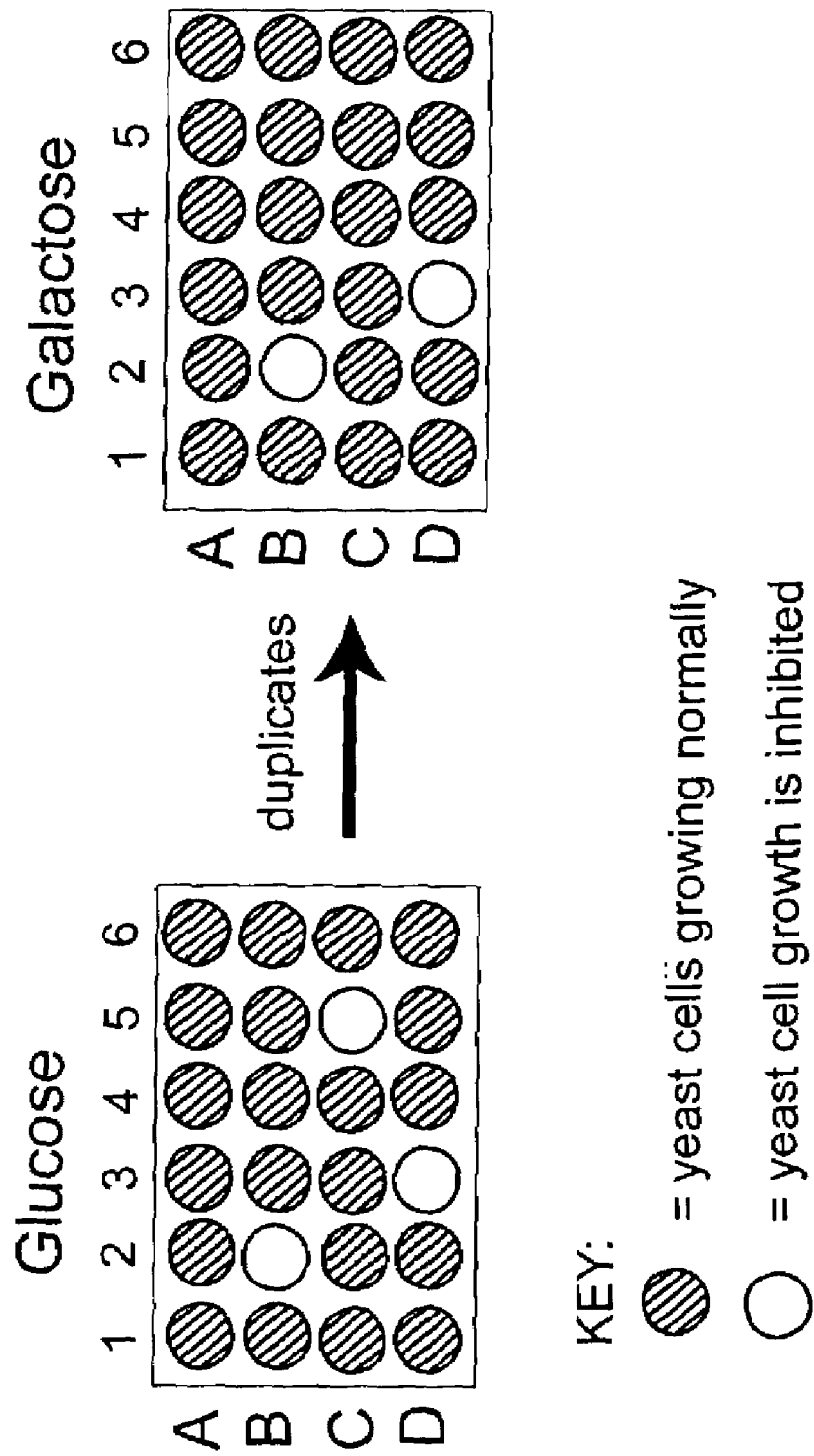
FIG. 3 shows a screen for CaESS1 or CaEss1 inhibitors (cultures of specially engineered *Saccharomyces cerevisiae* (see FIG. 2) are grown in duplicate plates under different conditions, e.g., one condition is glucose, another condition is galactose (or a mixture of glucose/galactose which produces low but sufficient levels of hPIN1 expression for cell viability, and this might be useful because massive overproduction of hPIN1, e.g., in galactose, might overcome compounds that inhibit both CaESS1 or CaEss1 and hPIN1 or PIN1, thus leading to possible false positives, i.e., possible compounds that inhibit both the fungal and human gene function); cells grown in glucose-containing medium express CaESS1 but not hPIN1; cells grown in galactose-containing medium express both CaESS1 and hPIN1; potential inhibitory compounds are applied to each well in duplicate, yeast growth is monitored; many compounds may have no effect, compounds in which yeast cell growth in both glucose and galactose plates (B2 and D3 in FIG. 3) inhibit both CaESS1 or CaEss1 and hPIN1 or hPIN1 and/or totally unrelated pathways (non-specific inhibitors of yeast cell growth). Compounds which inhibit yeast growth only in glucose plate (C5 in FIG. 3) are CaESS1 or CaEss1-specific inhibitors.
Figure 4:
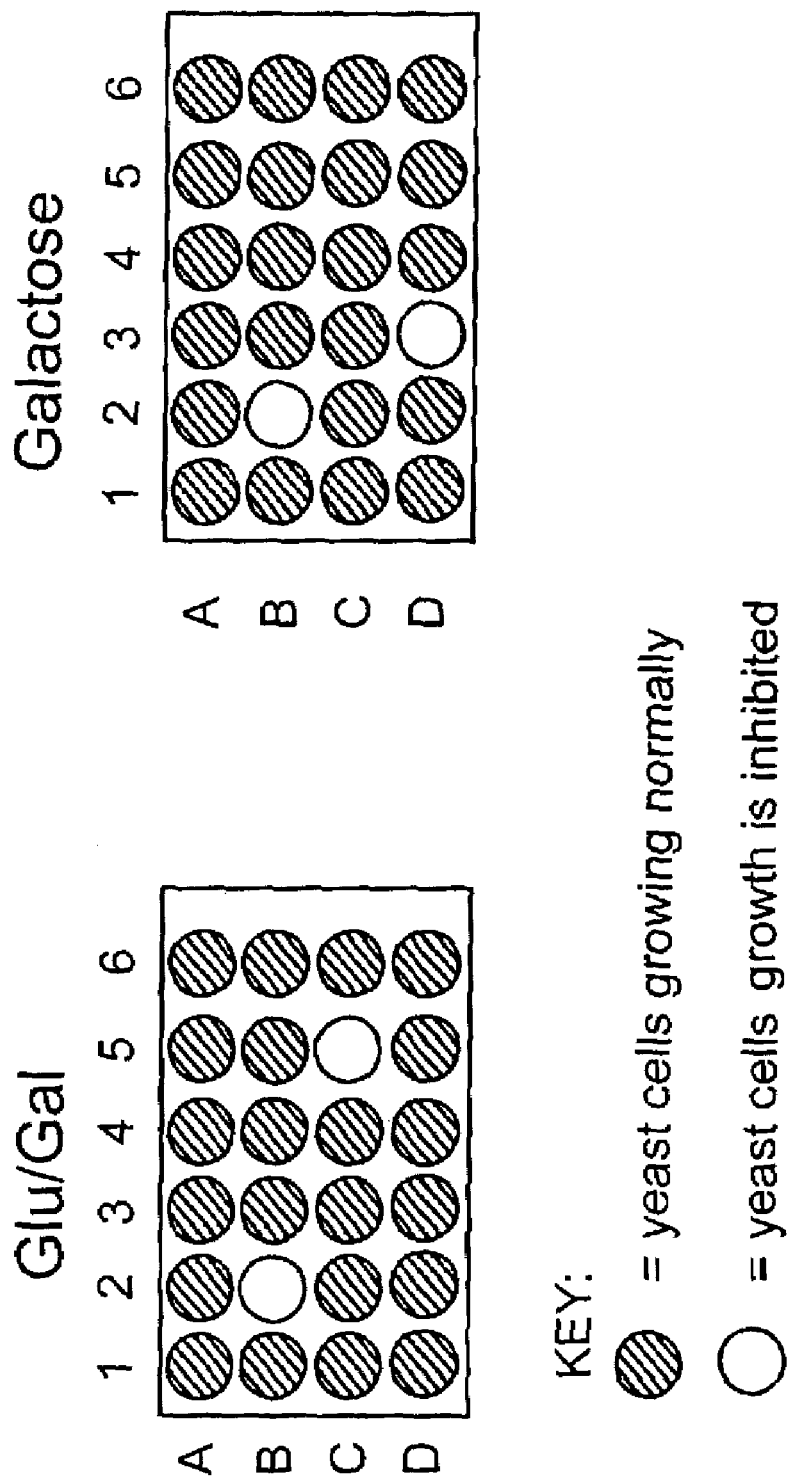
FIG. 4 shows a screen for hPIN1 or hPIN1 inhibitors (cultures of specially engineered *Saccharomyces cerevisiae* in which the ESS1 gene is deleted and a hPIN1 under the control of an inducible promoter (such as GAL1) is present are grown in duplicate plates under different conditions, e.g., one condition is to generate low levels of PIN1 sufficient for cell growth (e.g., glucose/galactose), another condition is to generate high levels of PIN1 (e.g., galactose); cells grown in medium containing a mixture of glucose/galactose express low levels of hPIN1; cells grown in galactose-containing medium express high levels of hPIN1; potential inhibitory compounds are applied to each well in duplicate, yeast growth is monitored; many compounds may have no effect, compounds in which yeast cell growth in both glucose/galactose and galactose plates (B2 and D3 in FIG. 4) non-specifically inhibit yeast cell growth, and compounds which inhibit only yeast growth in glucose/galactose plate (C5 in FIG. 4) are hPIN1 or hPIN1-specific inhibitors, as massive overproduction of hPIN1 (in galactose) overcomes the inhibitory effect (by titrating out the inhibitor).

Additionally or alternatively, a CaEss1 inhibitor can be a compound which selectively inhibits growth of S. cerevisiae not containing an endogenous ESS1 gene but rather CaESS1 and uninduced PIN1 (e.g., on a glucose medium) (see FIGS. 2, 3) and preferably does not inhibit or significantly inhibit PIN1, e.g., does not inhibit or significantly inhibit S. cerevisiae not containing an endogenous ESS1 gene but rather an induced PIN1 (e.g., on a glucose/galactose medium) (see FIG. 4).

Compositions which indeed inhibit PIN1 are nonetheless useful as antiproliferatives, e.g., antineoplastics, anti-tumor agents or anti-cancer agents.

Compositions containing inhibitors of CaEss1 or containing antiproliferatives are within the scope of the invention. Compositions for use in the invention can be prepared in accordance with standard techniques well known to those skilled in the pharmaceutical or medical arts. Such compositions can be administered in dosages and by techniques well known to those skilled in the medical arts taking into consideration such factors as the age, sex, weight, and condition of the particular patient, and the route of administration. The compositions can be administered alone, or can be co-administered or sequentially administered with other compositions of the invention or with other prophylactic or therapeutic compositions.

Examples of compositions of the invention include liquid preparations for orifice, e.g., oral, nasal, anal, genital (e.g., vaginal), etc., administration such as suspensions, syrups or elixirs; and, preparations for parenteral, subcutaneous, intradermal, intramuscular, intravenous, intraarterial, intralymphatic, or intraperitoneal administration (e.g., injectable administration) such as sterile suspensions or emulsions. In such compositions the active agent can be in admixture with a suitable carrier, diluent, or excipient such as sterile water, physiological saline, glucose or the like.

The compositions of the invention may be packaged in a single dosage form for injection administration or orifice administration. Accordingly, compositions in forms for such administration routes are envisioned by the invention. And again, the effective dosage and route of administration are determined by known factors, such as age, sex, weight, condition and nature of patient, as well as $LD_{50}$ and other screening procedures which are known and do not require undue experimentation. Dosages of each active agent can range from a few to a few hundred micrograms, e.g., 5 to 500 μg.

The compositions can be administered in intervals without undue experimentation by the skilled artisan considering the disclosure herein and the knowledge in the art and known factors such as age, sex, weight, condition, and nature of the patient as well as $LD_{50}$ and other screening procedure results; for instance, compositions can be administered in a regimen to or serially akin to administration protocols for known antifungals or antiproliferatives; or preferably over a shorter duration or in lesser doses than known antifungals or antiproliferatives.

Accordingly, the invention relates to diagnostic compositions and methods, as well as therapeutic or preventive compositions and methods.

A better understanding of the present invention and of its many advantages will be had from the following examples, given by way of illustration.

EXAMPLES

Example 1

CLONING CaESS1

The *Candida albicans* homolog of ESS1 was cloned by functional complementation of a temperature-sensitive *Saccharomyces cerevisiae* strain, ess1-L94P$^{ts}$. This strain was created by Applicants by methods described in Adachi et al., *Nucl. Acids Res.* 22:4229–4233, 1994, and is similar to temperature sensitive mutants of Hani et al., *J Biol Chem* Jan. 1, 1999; 274(1):108–16. Applicants screened a *Candida albicans* genomic DNA library to search for sequences capable of complementing the no-growth phenotype of the ess1-L94P$^{ts}$ strain under non-permissive conditions. The details are as follows.

A *Candida albicans* genomic DNA library in YEp352 was obtained from Navarro-Garcia (Mol. Cell Biol., 15, 2197–2206). The library carried 5–10 kb-sized genomic DNA fragments generated by Sau3A partial digestion of the *Candida albicans* 1001 genome and contained $2 \times 10^5$ independent members. The library was amplified in *Escherichia coli* 20-fold over the original size and purified prior to use.

The ess1-L94P$^{ts}$ yeast cells were transformed with a total of 200 μg of the amplified *Candida albicans* genomic library using a standard lithium acetate protocol (Ito et al., J. Bact. 53, 163–168). Transformation was done in 33 independent aliquots of 150 ul cells each using approximately 6 ug of library DNA. Based on the transformation efficiency (8300 transformants/μg), approximately $2 \times 10^6$ transformants (10-fold over library size) were expected. The 33 transformations were pooled in groups of three (11 pools; $1.5 \times 10^5$ transformants per pool) and grown overnight at 30° C. in 4 ml of CSM-minus-ura liquid medium. The cells were concentrated by centrifugation and plated onto CSM-minus-ura plates and incubated at 37° C. for 3 days. 150 colonies (i.e. positives) were obtained. The positives were serially passaged three times by streaking for single colonies and incubating at 37° C. for 3 days. Colonies representing 26 of the original 150 postives remained viable under these conditions.

To determine whether the complementing activity was plasmid-linked, these 26 postives were streaked onto 5-flouroorotic acid (5-FOA) containing plates at 37° C. 5-FOA selects against the URA3 gene carried on the library plasmids. Therefore, those positives that did not grow on 5-FOA plates carried complementing activity that was plasmid-linked. A total of 5 out of the 26 positives did not grow on 5-FOA plates at 37° C.; these were the desired clones.

Plasmids were rescued out of all 26 positives and retransformed into ess1-L94P$^{ts}$. Of these, only those 5 which had previously been shown to not grow on 5-FOA at 37° C. were able to rescue the no-growth phenotype of ess1-L94P$^{ts}$ at 37° C.

Restriction mapping of the 5 complementing clones revealed that they belonged to 2 different groups. Two clones comprising one group contained an identical ~8.5 Kb insert. DNA sequence analysis revealed the existence of an ESS1 homolog in *Candida albicans*. The amino acid identity to *Saccharomyces cerevisiae* ESS1 is 42%. The other group carried an unrelated *Candida albicans* high copy suppressor.

FIG. 1 shows the nucleotide sequence and predicted expression product from CaESS1. From this disclosure, a preferred method for cloning CaESS1 is by using PCR amplification employing primers derived from CaESS1 such as primers disclosed herein.

Example 2

CaEss1 Inhibitors

On the basis of Applicants' discovery of the CaESS1 gene and the fact that it is functionally equivalent to the *Saccharomyces cerevisiae* ESS1 gene, strains of *Saccharomyces cerevisiae* can be engineered for use in screens to identify chemical inhibitors of CaESS1 function. Such compounds can be used as antifungal drugs. Such compounds are identified based on their ability to block cell growth in *Saccharomyces cerevisiae* as a result of interference with CaESS1 function. This interference might or might not be due to direct inhibition of PPIase enzyme activity.

In addition, prior work demonstrated that the human ESS1 homolog (PIN1) is also a functionally equivalent to the *Saccharomyces cerevisiae* ESS1 gene (Lu el al., Nature 380, 544–547). Therefore, *Saccharomyces cerevisiae* strains can be engineered to conditionally express the products of both CaESS1 or human PIN1 in the same cells. Such strains can be used to identify inhibitor compounds that selectively inhibit CaESS1 function, but not human PIN1 function (or that inhibit PIN1 to a lesser degree). Finally, *Saccharomyces cerevisiae* strains expressing human PIN1 can be used in screens to identify compounds that inhibit human PIN1 function. These compounds can be antiproliferative (e.g. anticancer) drugs, and these compounds may also inhibit CaESS1 function.

Figure 2:
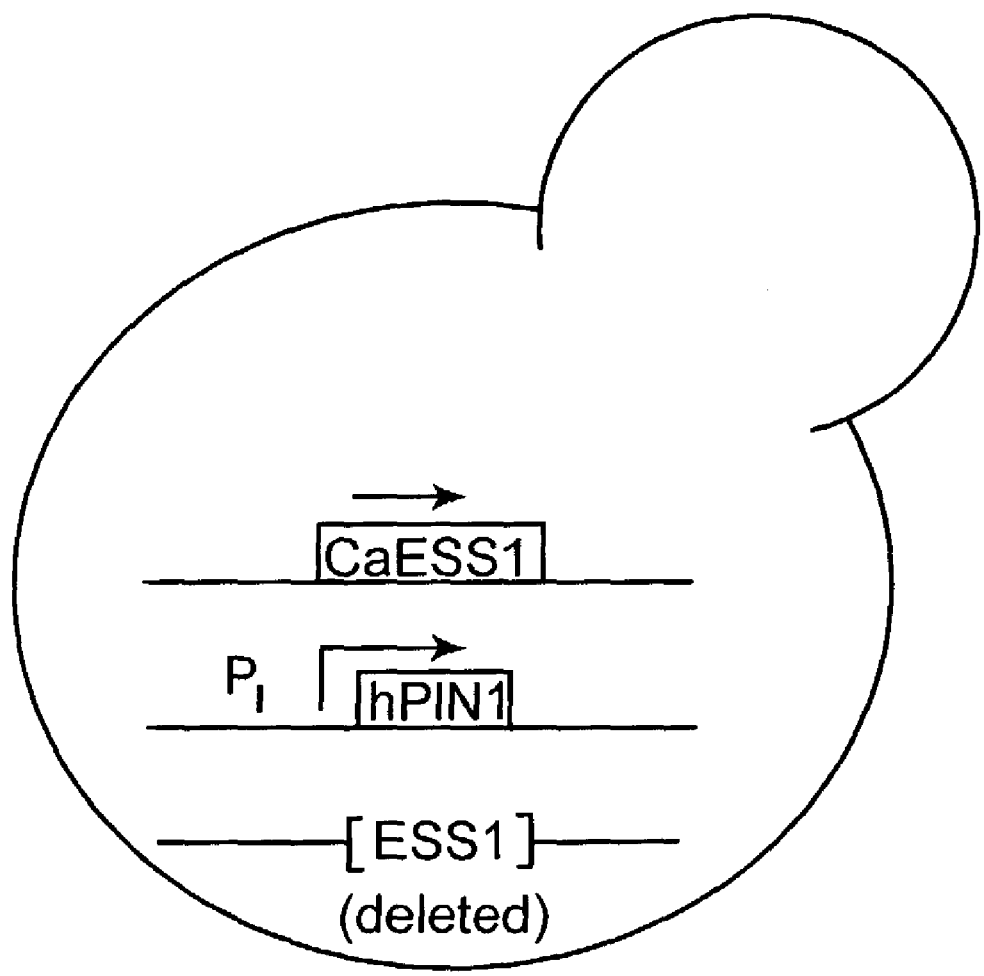
FIG. 2 shows the strategy for identifying inhibitors specific for *Candida albicans* CaEss1 (the yeast *Saccharomyces cerevisiae* is engineered to express both the *Candida albicans* CaESS1 gene and the human PIN1 gene; the endogenous *Saccharomyces cerevisiae* gene is deleted; the hPIN1 gene is expressed from an inducible promoter (e.g., the GAL1 promoter) so that it can be turned off and on by changes in the culture medium (strains can also bear other changes such as mutations that favor higher efficiency drug entry or retention and the CaESS1 gene might be modified so as to make it more sensitive to the effects of chemical inhibitors, for example, by the introduction of conditional-lethal mutations, as the use of such mutations, e.g., temperature-sensitive mutations, for screens carried out under permissive or semi-permissive conditions would sensitize cells to the effects of CaESS1 or CaEss1 inhibitors))

A representative example of the general design of such strains and how the inhibitor screens work are shown in FIGS. 2, 3, and 4. Note: The strategies outlined here are easily adaptable to screen for inhibitors of potential ESS1 homologs from other pathogenic fungi, e.g. *Cryptococcus neoformans* or *Aspergillus fumigatus*.

FIG. 2 shows the strategy for identifying inhibitors specific for *Candida albicans*. The yeast *Saccharomyces cerevisiae* is engineered to express both the *Candida albicans* CaESS1 gene and the human PIN1 gene. The endogenous *Saccharomyces cerevisiae* ESS1 gene is deleted. The hPIN1 gene is expressed from an inducible promoter (e.g., the GAL1 promoter) so that it can be turned off and on by changes in the culture medium (strains can also bear other changes such as mutations that favor higher efficiency drug entry or retention and the CaESS1 gene might be modified so as to make it more sensitive to the effects of chemical inhibitors, for example, by the introduction of conditional-lethal mutations, as the use of such mutations, e.g., temperature-sensitive mutations, for screens carried out under permissive or semi-permissive conditions would sensitize cells to the effects of CaESS1 or CaEss1 inhibitors).

FIG. 3 shows a screen for CaESS1 or CaEss1 inhibitors. Cultures of specially engineered *Saccharomyces cerevisiae* (see FIG. 2) are grown in duplicate plates under different conditions, e.g., one condition is glucose, another condition

Example 3

CaEss1 Amplification; Primers Therefor

The DNA oligonucleotide primers, OW-216 AND OW-221, are based on the CaESS1 sequence, and preferentially amplify CaESS1 in a diagnostic PCR reaction. The reaction product is a 453 bp of DNA that corresponds to a portion of the CaESS1 open reading frame. These primers will not amplify human PIN1, or *Saccharomyces cerevisiae* ESS1 sequences (the corresponding sequences from PIN1 and ESS1 are shown below the CaESS1 primers; they are clearly different).

```
OW-216 5' CCA-GAT-GGT-ATA-AGT-AGA-AC-   (C albicans CaESS1) (SEQ ID NO:3)
       3'

5' ATC-AAC-GGC-TAC-ATC-CAG-AA-   (human PIN1)        (SEQ ID NO:4)
       3'

5' GAC-GCT-ACG-GAC-GAA-CTG-AA-   (S. cerevisiae ESS1)(SEQ ID NO:5)
       3'

OW-221 5' CAA-TGA-CGG-GAA-ACG-TTC-CG-   (C. albicans CaESS1)(SEQ ID NO:6)
       3'

5' GGG-AGT-GGG-GAC-CCC-AGG-GC-   (human PIN1)        (SEQ ID NO:7)
       3'

5' GTC-ATC-TGG-AGA-GGA-AAA-GA-   (S. cerevisiae ESS1)(SEQ ID NO:8)
       3'
``` is galactose (or a mixture of glucose/galactose which produces low but sufficient levels of hPIN1 expression for cell viability, and this might be useful because massive overproduction of hPIN1, e.g., in galactose, might overcome compounds that inhibit both CaESS1 or CaEss1 and hPIN1 or PIN1, thus leading to possible false positives, i.e., possible compounds that inhibit both the fungal and human gene function). Cells grown in glucose-containing medium express CaESS1 but not hPIN1; cells grown in galactose-containing medium express both CaESS1 and hPIN1; potential inhibitory compounds are applied to each well in duplicate, yeast growth is monitored. Many compounds may have no effect. Compounds in which yeast cell growth in both glucose and galactose plates (B2 and D3 in FIG. 3) inhibit both CaESS1 or CaEss1 and hPIN1 or hPIN1 (non-specific inhibitors of yeast cell growth); and, compounds which inhibit only yeast growth in glucose plate (C5 in FIG. 3) are CaESS1 or CaEss1-specific inhibitors.

FIG. 4 shows a screen for hPIN1 or hPIN1 inhibitors. Cultures of specially engineered *Saccharomyces cerevisiae* in which the ESS1 gene is deleted and a hPIN1 under the control of a promoter such as GAL1 is present are grown in duplicate plates under different conditions, e.g., one condition is a mixture of glucose and galactose, another condition is galactose; cells grown in medium containing a mixture of glucose/galactose express low levels of hPIN1; cells grown in galactose-containing medium express high levels of hPIN1; potential inhibitory compounds are applied to each well in duplicate, yeast growth is monitored. Many compounds may have no effect. Compounds in which yeast cell growth in both glucose/galactose and galactose plates (B2 and D3 in FIG. 4) non-specifically inhibit yeast cell growth; and compounds which inhibit only yeast growth in glucose/galactose plate (C5 in FIG. 4) are hPIN1 or hPIN1 inhibitors, as massive overproduction of hPIN1 (in galactose) overcomes the inhibitory effect by titrating out the inhibitor.

TABLE 1

Results of gene knockout of CaESS1 in *Candida albicans*.

| Transformation of caess1/CaESS1* | # Transformants analyzed | Method of analysis | Locus of insertion |
|---|---|---|---|
| CaGD-1 | 11 | Southern + PCR | 1st allele |
| " | 19 | PCR | 1st allele |
| CaGD-2 | 11 | Southern + PCR | 1st allele |
| " | 19 | PCR | 1st allele |
| total | 60 | | 60/60 in 1st allele |

*CaGD-1 and CaGD-2 represent independently-derived 5-FOA revertants from different CAI4-disrupted strains (hisG-CaURA3-hisGΔCaESS1).

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Arevalo-Rodriguez, M., Cardenas, M. E., Wu, X. Hanes, S. D., and Heitman, J. (2000). Cyclophilin A suppresses mutations in the Ess1 prolyl isomerase via common targets required for mitosis. (submitted).
2. Dolinski, K., Muir, S., Cardenas, M. and Heitman, J. (1997). All cyclophilins and FK506 binding proteins are, individually and collectively, dispensable for viability in *Saccharomyces cerevisiae*. Proc. Natl. Acad. Sci. USA 94, 13093–13098.
3. Fonzi, W. A. and Irwin, M. Y. (1993). Isogenic strain construction and gene mapping in *Candida albicans*. Genetics 134, 717–728.

4. Fujimori, F., Takahash, K., Uchida, C., and Uchida, T. (1999). Mice lacking pin1 develop normally, but are defective in entering cell cycle from G(0) arrest. Biochem. Biophys. Res. Commun. 265, 658–663.

5. Georgopapadakou, N. H. and Walsh, T. J. (1994). Human mycoses: Drugs and targets for emerging pathogens. Science 264, 371–373.

6. Hanes, S. D. (1988). Isolation, sequence and mutational analysis of ESS1, a gene essential for growth in *Saccharomyces cerevisiae*. Ph.D. Thesis, Brown University.

7. Hanes, S. D., Shank, P. R., and Bostian, K. A. (1989). Sequence and mutational analysis of ESS1, a gene essential for growth in *Saccharomyces cerevisiae*. Yeast 5: 55–72.

8. Hemenway, C. and Heitman, J. (1993). Proline isomerases in microorganisms and small eukaryotes, p. 38–46. In A. C. Allison, K. J. Lafferty and H. Fliri Eds., Immunosuppressive and Anti inflammatory Drugs. The New York Academy of Sciences, New York. vol. 696.

9. Lu, K. P., Hanes, S. D. and Hunter, T. (1996). A human peptidyl-prolyl isomerase essential for regulation of mitosis. Nature 380, 544–547.

10. Maleszka, R., Hanes, S. D., Hackett, R. L., De Couet, H. G., and Miklos, G. L. G. (1996). The *Drosophila melanogaster* dodo (dod) gene, conserved in humans, is functionally interchangeable with the ESS1 cell division gene of *Saccharomyces cerevisae*. Proc. Natl. Acad. Sci. USA. 93, 447–451.

11. Morris, D. P., Phatnani, H. P., and Greenleaf, A. L. (1999). Phospho-carboxyl-terminal domain binding and the role of prolyl isomerase in pre-mRNA 3'-end formation. J. Biol. Chem. 274, 31583–31587.

12. Rudd, K. E., Sofia, H. J. and Koonin, E. V. (1995). A new family of peptidyl-prolyl isomerases. Trends in Biochemical Sciences 20,12–14.

13. Shen M., Stukenberg P. T., Kirschner M. W., and Lu K. P. (1998). The essential mitotic peptidyl-prolyl isomerase Pin1 binds and regulates mitosis-specific phosphoproteins. Genes Dev. 12, 706–720.

14. Sudol, M. (1996). Structure and function of the WW domain. Prog. Biophys. Mol. Biol. 65, 1113–132.

15. Wu, X., Wilcox, C. B., Devasahayam, G., hackett, R. L., Arevalo-Rodriguex, M., Cardenas, M. E., and Hanes, S. D. (2000). The mitotic Ess1 (Pin1) prolyl-isomerase is linked to chromatin remodeling complexes and the general transcription machinery. (submitted).

Sequence Listing

What is claimed is:

1. A method for preparing the protein encoded by the sequence, SEQ.ID.NO:10, a *Candida albicans* Essential 1 (CaESS 1) gene, comprising inserting an isolated or purified nucleic acid molecule consisting of the nucleotide sequence of SEQ ID NO: 10 into an isolated recombinant expression vector, wherein the vector is inserted into an isolated host ceil and the cell is cultured under appropriate conditions, thereby preparing the protein encoded by the CaESS 1 gene.

2. The method of claim 1 wherein the isolated host cell is a yeast.

3. The method of claim 1, wherein the isolated recombinant expression vector is a poxvirus, baculovirus, herpesvirus, adenovirus, lentiviral, or DNA plasmid.

* * * * *

UNITED STATES PATENT AND TRADEMARK OFFICE
CERTIFICATE OF CORRECTION

PATENT NO. : 7,217,538 B2  Page 1 of 1
APPLICATION NO. : 10/342555
DATED : May 15, 2007
INVENTOR(S) : Steven D. Hanes, Gina Devasahayam and Vishnu Chaturvedi It is certified that error appears in the above-identified patent and that said Letters Patent is hereby corrected as shown below:

In the Claims:

Line 25, column 26, please correct "ceil" to --cell--.

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,217,538 B2 | |
| APPLICATION NO. | : 10/342555 | |
| DATED | : May 15, 2007 | |
| INVENTOR(S) | : Steven D. Hanes, Gina Devasahayam and Vishnu Chaturvedi | |

It is certified that error appears in the above-identified patent and that said Letters Patent is hereby corrected as shown below:

On the Title Page:

Correct assignee's address to --Rensselaer, NY--.

In the Specification:

Column 9, Line 64, please correct "CAESS1" to --CaESS1--;

Column 17, Line 66, please correct "postives" to --positives--;

Column 18, Line 2, please correct "postives" to --positives--;

Column 20, Lines 56-59, please update the reference cited to read

--Arévalo-Rodriguez, M., Cardenas, M., Wu, X., Hanes, S.D., and Heitman, J. (2000). Cyclophilin A and Ess1 interact with and regulate silencing by the Sin3-Rpd3 histone deacetylase. EMBO J. 19: 3739-3749--;

UNITED STATES PATENT AND TRADEMARK OFFICE
CERTIFICATE OF CORRECTION

PATENT NO.        : 7,217,538 B2
APPLICATION NO.   : 10/342555
DATED             : May 15, 2007
INVENTOR(S)       : Steven D. Hanes, Gina Devasahayam and Vishnu Chaturvedi It is certified that error appears in the above-identified patent and that said Letters Patent is hereby corrected as shown below:

Column 22, Lines 15-24, please update the reference cited to read --Wu, X., Wilcox, C.B., Devasahayam, G., Hackett, R.L., Arévalo-Rodriguez, M., Cardenas, M., Heitman, J., and Hanes, S.D. (2000). The Ess1 prolyl-isomerase is linked to chromatin remodeling complexes and the general transcription machinery. EMBO J. 3727-3738--.

Signed and Sealed this

Thirteenth Day of May, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,217,538 B2 | Page 1 of 1 |
| APPLICATION NO. | : 10/342555 | |
| DATED | : May 15, 2007 | |
| INVENTOR(S) | : Steven D. Hanes et al. | |

It is certified that error appears in the above-identified patent and that said Letters Patent is hereby corrected as shown below:

IN THE SPECIFICATION

Column 1, line 11, please replace the paragraph as follows:

"STATEMENT OF GOVERNMENT INTEREST

Without any prejudice or admission, this invention may have been made with funding from the National Institutes of Health, HRI grant #815-3487, such that the U.S. Government may have certain rights."

--STATEMENT REGARDING FEDERALLY SPONSORED RESEARCH OR DEVELOPMENT

This invention was made with government support under Grant No. 1R01GM55108-01A1 awarded by the National Institutes of Health. The government has certain rights in the invention.--

Signed and Sealed this
Twenty-fourth Day of April, 2012

David J. Kappos
*Director of the United States Patent and Trademark Office*